United States Patent [19]

Taga et al.

[11] 4,055,617
[45] Oct. 25, 1977

[54] PROCESS FOR PREPARING GRANULAR POTASSIUM SORBATE

[75] Inventors: Yasuyoshi Taga; Masaharu Wakasone, both of Ogaki, Japan

[73] Assignee: Nippon Gohsei Kagaku Kogyo Kabushiki Kaisha, Osaka, Japan

[21] Appl. No.: 678,983

[22] Filed: Apr. 21, 1976

[30] Foreign Application Priority Data

Apr. 26, 1975  Japan .................................. 50-50909

[51] Int. Cl.$^2$ ............................................. C07C 57/10
[52] U.S. Cl. .................................. 264/141; 264/143; 264/170; 264/330; 260/526 N
[58] Field of Search ................... 264/142, 143, 176 R, 264/141, 330, 170; 260/526 N; 425/67, 311, 378 S, 379 S

[56] References Cited

PUBLICATIONS

Feiser et al., *Organic Chemistry*, p. 169 (1956).

*Primary Examiner*—Robert F. White
*Assistant Examiner*—John A. Parrish
*Attorney, Agent, or Firm*—Armstrong, Nikaido & Marmelstein

[57] ABSTRACT

A process for preparing granular potassium sorbate by adding water or a mixture of water and an organic solvent to powdery potassium sorbate, kneading the resulting mixture under specific conditions to give a uniformly wetted powder, supplying the wetted powder to a screw type extruding machine, extruding the wetted powder through a perforated-cylinder die under specific conditions to give a vermicelli-like extrudate, and drying the extrudate.

2 Claims, No Drawings

PROCESS FOR PREPARING GRANULAR POTASSIUM SORBATE

BACKGROUND OF THE INVENTION

The present invention relates to a process for preparing granular potassium sorbate.

In general, potassium sorbate is prepared by reacting sorbic acid with potassium hydroxide or a potassium salt such as potassium carbonate in a medium of water or an organic solvent, and then recovered from the reaction mixture by means of recrystallization, spray drying or drum drying. The thus prepared potassium sorbate is obtained in a form of crystalline powder.

Potassium sorbate has excellent antifungal activity and nontoxicity, and has been effectively employed as a preservative for foods such as a fish-paste product or cheese. However, when a powder of potassium sorbate is employed in such a use, workability is not so good compared with granule. For instance, the fine powder is easy to scatter in handling. Also, when the powder is dissolved in water, it remains floated on the surface and does not dissolve quickly.

For the purpose of solving such problems, it has been proposed to granulate the powdery potassium sorbate. As a preferred granule, it is required to be so rigid that the granule is not broken even under load or friction during transportation, and to have good solubility in water. Also, it is desirable that the granule does not contain a binder because of lowering the quality of the granule, and that the granule is prepared in high yield.

As a practical process, a process for preparing granular potassium sorbate by wetting powders of potassium sorbate with water or an organic solvent and applying it to a granulator such as vibration type or extrusion type is proposed. For instance, there is disclosed in U.S. Pat. No. 3,758,563 a process for producing granular potassium sorbate by wetting powdery potassium sorbate with water or a mixture of water and an organic solvent, molding it with particular types of extruding granulators and drying it. According to the process, however, particular types of extruding granulators wherein not only extruding force but also lateral stress are applied to the wetted powder must be employed.

OBJECTS OF THE INVENTION

It is an object of the present invention to provide an improved process for preparing granular potsssium sorbate.

A further object of the invention is to provide a process for preparing granular potassium sorbate having excellent physical properties by employing conventional extruding machine.

These and other objects of the invention will become apparent from the description hereinafter.

DETAILED DESCRIPTION

It has now been found that the above-mentioned objects can be attained by adding water or a mixture of water and an organic solvent to powdery potassium sorbate, kneading the resulting mixture to give uniformly wetted powder, supplying the wetted powder to a conventional extruding machine, extruding the wetted powder through a perforated-cylinder die under specific conditions to give a vermicelli-like extrudate, and drying the extrudate.

In the process of the present invention, water alone or a mixture of water and an organic solvent is first added to the crystalline powder of potassium sorbate. The amount of water is selected from the range of 2 to 8% by weight based on the weight of dry potassium sorbate. In general, the less the amount of water employed, the easier the drying. However, less than 2% by weight of water results in breakdown or choking of die. On the other hand, when the amount of water is more than 8% by weight, the wetted powder has a tendency to stick and troubles such as flowage occur during the kneading and extruding step, and the obtained granules are bulky and fragile. According to the invention, an organic solvent in an amount of not more than 15% by weight based on the weight of potassium sorbate may be employed in combination with water. The employment of the combination of water and an organic solvent makes drying easy and has the advantage that the blocking of the vermicelli-like extrudate is decreased. When the crystalline powder of potassium sorbate prepared in an organic solvent is employed, the powder containing the organic solvent may be employed without completely removing the organic solvent. The organic solvents employed in the invention are those having a boiling point of not more than 100° C. which are inactive with potassium sorbate. Examples of the organic solvent are methanol, ethanol, isopropanol and acetone. In the present invention, as a result of wetting the powdery potassium sorbate with the above-mentioned specific amount of water or a mixture of water and an organic solvent, granules having sufficient rigidity can be obtained without employing any binder such as starch or carboxy methyl cellulose.

The thus obtained mixture of the powdery potassium sorbate and water or water-organic solvent is then sufficiently kneaded at a temperature of 10° l to 45° C. for 10 minutes to 4 hours. As a kneading machine, any conventional kneader or a known high speed mixer such as Henschel type, gyratory-screw type or ribbon type mixer may be employed. The kneading step is essential for the present invention in order to get uniformly wetted powder, and it makes possible to employ a conventional extruding machine. Besides, the bulk density of the granule is increased by sufficient kneading, and extruding by conventional extruding machine can be smoothly carried out without bridging in a die. When the kneading step is omitted in the present invention, fragile chips are extruded and troubles such as choking of die occur. Furthermore, the bulk density and rigidity of the so prepared granules are low, and the desired granules can not be obtained. Upon carrying out the kneading, the temperature is selected from the range of 10° to 45° C. When the kneading is carried out at a temperature of more than 45° C., blocking occurs on walls of a kneading machine and the wetted powder is colored. Further, the kneading must be carried out at least for 10 minutes. However, even if the kneading is carried out for over 4 hours, the effects of kneading do not increase and, on the contrary, air is apt to be mixed, whereby the operation efficiency is lowered.

After the kneading step, the wetted powder is supplied to a conventional extruding machine. The conventional extruding machine in the present invention means a screw type extruding machine, in which only an extruding force is applied to the wetted powder and a lateral force at a die is not required. As such a screw type extruding machine, a usual extruding granulator equipped with one or more screws and a die at the vicinity of the end of the screw may be employed. For instance, a screw type extruding machine disclosed in Japanese patent publication No. 18202/1965 may be employed. These conventional extruding machines have good workability due to their simple mechanism and give high yield of granule.

The use of a conventional extruding machine in the extruding step is one of the features of the present invention, and can be attained by the combination of the addition step of water or its mixture and the kneading step.

It is necessary to carry out the extruding under an extruding pressure at a die of 10 to 50 kg./cm$^2$., and an extruding rate at a die of 1 to 4 g./cm$^2$.sec. When the pressure is less than 10 kg./cm$^2$., the obtained granules have low bulk density and are fragile. Further, when the extruding rate is lower than 1 g./cm$^2$.sec., the choking of the die occurs, and when the extruding rate is higher than 4 g./cm$^2$.sec., there is a tendency that the extrudate sticks with each other.

The potassium sorbate extruded through a perforated-cylinder die in a form like vermicelli in length of 30 to 40 cm. are then dried on the wire net by contacting with a hot air. The extrudate is cut into granules in length of not more than several millimeters in the drying step. The drying is carried out so as to reduce the content of volatile material to not more than 0.1% by weight. A fluidized bed drier equipped with a crusher on the bed may also be employed.

The granular potassium sorbate obtained by the present invention is usually columnar grains in a diameter of 0.5 to 5 mm. in a length of 2 to 5 mm. and has a bulk density in a range of 0.6 to 0.7.

The present invention is more specifically described and explained by means of the following Examples.

EXAMPLE 1

A Nauta mixer, one of the gyratory-screw type mixers, was charged with 100 kg. of powder potassium sorbate of which water content was less than 1% by weight and 6 kg. of water, and the kneading was carried out at a temperature of 35° C. for one hour. Then, the thus obtained mixture was supplied to a hopper of 7.5-horsepower single screw type extruding machine, and was extruded in a form like vermicelli through a die which had a thousand of round openings having a diameter of 1 mm. by means of a screw which rotated at a speed of 15 r.p.m. under an extruding pressure at a die of 25 kg./cm$^2$., and an extruding rate at a die of 3.5 g./cm$^2$.sec. The amount of the mixture extruded was 100 kg. per hour. The thus extruded potassium sorbate in a form like vermicelli was dropped onto a wire net which was gyrating, and was dried by blowing a hot air at a temperature of 50° C. from below the wire net. On the wire net, the extrudate was spontaneously cut into columnar grains having a length of 2 to 4 mm.

The bulk density, T value and solubility of the thus obtained granules were 0.6, 95.0% and 50 sec., respectively.

The T value is a value corresponding to the photo-transmission measured with a spectrophotometer at 430 m μ wave length through a cell of 1 cm. thickness containing a 20% by weight aqueous solution of the granular potassium sorbate, represented by percent, as compared with the photo-transmission through the same cell containing water.

The solubility is the time in seconds required to completely dissolve 20 g. of the granular potassium sorbate poured into 100 ml. of water without agitation.

EXAMPLE 2

Potassium sorbate obtained by recrystallization from an isopropanol solution containing 15% by weight of water was separated by means of centrifugation to give a cake containing 10% by weight of volatile material. A Nauta mixer was charged with 100 kg. of the cake and 2 kg. of water, and the kneading was carried out at a temperature of 40° C. for 3 hours. Then, the thus obtained mixture was supplied to a 25-horsepower single screw type extruding machine, and was extruded in a form like vermicelli through a die which had five thousands of round openings having a diameter of 1 mm. by means of a screw which rotated at a speed of 33 r.p.m. under an extruding pressure at a die of 30 kg./cm$^2$., and an extruding rate at a die of 2.8 g./cm$^2$.sec. The amount of the mixture extruded was 400 kg. per hour. The thus extruded potassium sorbate in a form like vermicelli was dropped into a through-flow dryer having a wire net of 60 meshes to pre-dry it, and was then dried in a fluidized bed dryer to reduce the volatile material content to not more than 0.1% by weight.

The thus obtained potassium sorbate was columnar grains having a diameter of 1 mm. and a length of 2 to 5 mm. The bulk density, T value and solubility of the granules were 0.65, 97% and 40 sec., respectively.

COMPARATIVE EXAMPLE 1

The same procedure as in Example 2 was repeated except that the kneading time was cut down to 5 minutes. The choking of die occured, and the extruding capacity was reduced to 100 kg. per hour. Also, the extruded potassium sorbate was fragile and the large amount of fine powder was produced, and therefore the yield of granules was low. The bulk density of the granules was 0.5.

COMPARATIVE EXAMPLE 2

The same procedure as in Example 2 was repeated except that water was added to 100 kg. of the cake in an amount of 8 kg. (in an amount of about 10% by weight based on the weight of potassium sorbate) instead of 2 kg. The amount of the mixture extruded was 800 kg. per hour. There was observed the blocking of the extrudate in the pre-drying apparatus. Also the obtained granules were very fragile.

What we claim is:
1. A process for preparing granular potassium sorbate, which comprises the steps of
    a. adding water to powdery potassium sorbate in an amount of 2 to 8% by weight based on the weight of the potassium sorbate,
    b. kneading the resulting mixture at a temperature of 10° to 45° C. for 10 minutes to 4 hours to give a uniformly wetted powder,
    c. supplying the wetted powder to a hopper of a screw type extruding machine equipped with a perforated cylinder die at a vicinity of an end of a screw, and extruding it under an extruding pressure at said die of 10 to 50 kg./cm$^2$., and an extruding rate at said die of 1 to 4 g./cm$^2$.sec. to give a vermicelli-like extrudate, and
    d. drying the extrudate to give granules having a volatile material content of not more than 0.1% by weight.
2. The process of claim 1, wherein an organic solvent selected from the group consisting of methanol, ethanol, isopropanol and acetone was further added to powdery potassium sorbate in an amount of not more than 15% by weight based on the weight of the potassium sorbate.

* * * * *